United States Patent
Hancu et al.

(10) Patent No.: US 9,513,354 B2
(45) Date of Patent: Dec. 6, 2016

(54) DETERMINING ELECTRICAL PROPERTIES OF TISSUE USING COMPLEX MAGNETIC RESONANCE IMAGES

(71) Applicant: General Electric Company, Schenectady, NY (US)

(72) Inventors: Ileana Hancu, Clifton Park, NY (US); Selaka Bandara Bulumulla, Niskayuna, NY (US); Seung-Kyun Lee, Cohoes, NY (US)

(73) Assignee: General Electric Company, Niskayuna, NY (US)

(*) Notice: Subject to any disclaimer, the term of this patent is extended or adjusted under 35 U.S.C. 154(b) by 1025 days.

(21) Appl. No.: 13/652,155

(22) Filed: Oct. 15, 2012

(65) Prior Publication Data
US 2014/0103925 A1 Apr. 17, 2014

(51) Int. Cl.
*G01R 33/48* (2006.01)
*G01R 33/32* (2006.01)
*A61B 5/055* (2006.01)

(52) U.S. Cl.
CPC .............. *G01R 33/48* (2013.01); *A61B 5/055* (2013.01)

(58) Field of Classification Search
CPC ..... G01R 33/246; G01R 33/48; G01R 33/288; A61B 5/055; A61B 5/4869
USPC .......................... 324/300–322; 600/407–421
See application file for complete search history.

(56) References Cited

U.S. PATENT DOCUMENTS

| | | | |
|---|---|---|---|
| 5,995,863 A | 11/1999 | Farace et al. | |
| 7,259,558 B2 | 8/2007 | Bieri et al. | |
| 8,076,939 B2 | 12/2011 | Setsompop et al. | |
| 8,942,931 B2* | 1/2015 | Bulumulla | 324/309 |
| 2009/0322331 A1* | 12/2009 | Buracas | A61B 5/0263 324/309 |
| 2012/0139541 A1 | 6/2012 | Weiss et al. | |
| 2012/0146637 A1* | 6/2012 | Zhu | G01R 33/48 324/307 |
| 2012/0306493 A1* | 12/2012 | Voigt | A61B 5/0536 324/309 |

FOREIGN PATENT DOCUMENTS

WO 2011086512 A1 7/2011

OTHER PUBLICATIONS

Van de Moortele, Pierre-François, et al. "Calibration tools for RF shim at very high field with multiple element RF coils: from ultra fast local relative phase to absolute magnitude B1+ mapping." Proc Intl Soc Mag Reson Med. vol. 15. 2007.*

(Continued)

*Primary Examiner* — Melissa Koval
*Assistant Examiner* — Rishi Patel
(74) *Attorney, Agent, or Firm* — Melissa K. Dobson

(57) ABSTRACT

Exemplary embodiments are directed to estimating an electrical property of tissue using Magnetic Resonance (MR) images. In exemplary embodiments, complex MR images of a target tissue are obtained. An estimated value of an electrical property of the target tissue is determined based on complex values of the pixels in the complex MR images. The complex values are proportional to the product of the transmit radio frequency magnetic field and the receive RF magnetic field.

16 Claims, 6 Drawing Sheets

(56) References Cited

OTHER PUBLICATIONS

Joines et al., "A Comparison Using Tissue Electrical Properties and Temperature Rise to Determine Relative Absorption of Microwave Power in Malignant Tissue", Medical Physics, vol. 16, Issue 6, pp. 840-844, Nov.-Dec. 1989.

Farace et al., "An Automated Method for Mapping Human Tissue Permittivities by MRI in Hyperthermia Treatment Planning", Physics in Medicine and Biology, vol. 42, Issue 11, 1997.

Novotny et al., "Assessment of the Accuracy of Stereotactic Target Localization Using Magnetic Resonance Imaging: A Phantom Study", Journal of Radiosurgery, vol. 1, Issue 2, pp. 99-111, 1998.

Yang et al., "Manipulation of Image Intensity Distribution At 7.0 T: Passive RF Shimming and Focusing With Dielectric Materials", Journal of Magnetic Resonance Imaging, vol. 24, Issue 1, pp. 197-202, Jul. 2006.

Zhang et al., "Imaging Electrical Properties of the Human Brain Using a 16-channel Transceiver Array Coil at 7T", Proceedings of the International Society for Magnetic Resonance in Medicine, vol. 19, pp. 126, 2011.

Geeter et al., "A DTI-based Model for TMS using the Independent Impedance Method with Frequency-dependent Tissue Parameters", Physics in Medicine and Biology, vol. 57, Issue 8, pp. 2169-2188, Apr. 21, 2012.

\* cited by examiner

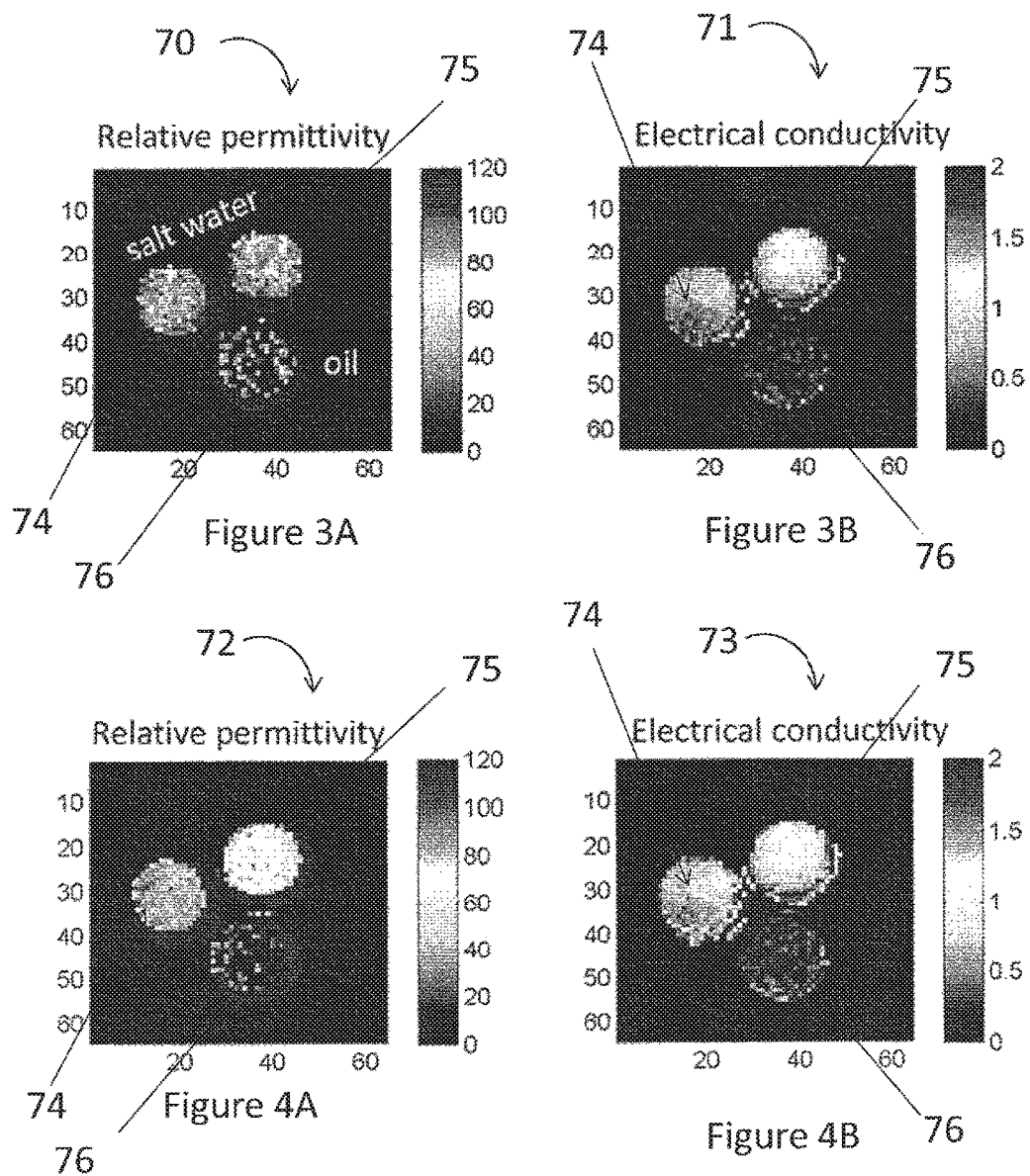

DETERMINING ELECTRICAL PROPERTIES OF TISSUE USING COMPLEX MAGNETIC RESONANCE IMAGES

STATEMENT AS TO FEDERALLY SPONSORED RESEARCH & DEVELOPMENT

This invention was made with Government support under contract number R01CA154433 awarded by the National Institutes of Health through the National Institute of Biomedical Imaging and Bioengineering. The Government has certain rights in the invention.

BACKGROUND

Magnetic Resonance Imaging (MRI) or Nuclear Magnetic Resonance (NMR) imaging generally provides spatial discrimination of resonant interactions between radio frequency (RF) waves and atomic nuclei in a magnetic field. Specifically, MRI utilizes hydrogen nuclear spins of the water molecules in the human body, which are polarized by a strong, uniform, static magnetic field, commonly referred to as $B_0$ or the main magnetic field. When a substance, such as human tissue, is subjected to the main magnetic field, the individual magnetic moments of the spins in the tissue attempt to align with the main magnetic field. When excited by an RF wave, the spins precess about the main magnetic field at a characteristic Larmor frequency. Signals are emitted by the excited spins, which are processed to generate Magnetic Resonance (MR) images of the subject.

The electrical properties of substances, such as human tissue, determine their interaction with the radio-frequency fields used in MRI, are useful to know for certain reasons, and could be measured from MRI exams. For example, determination of the electrical properties of tissue (conductivity and permittivity) are useful in estimating local RF power deposition (also known as local specific absorption rate or abbreviated as SAR) during acquisition of MR images. The electrical properties of tissue can also be useful in discriminating between malignant and healthy tissue (e.g., malignant tissue has been shown to have higher permittivity and conductivity than surrounding healthy tissue). In some applications, knowledge of the electrical properties of tissue can be used during therapeutic applications of heat using radio frequency, e.g., RF hyperthermia for treatment planning.

Determining the electrical properties of tissue in-vivo using MRI has posed several problems due to the inability to directly measure the complex values (magnitude and phase) of the receive RF magnetic field $B_1^-$ and the transmit RF magnetic field $B_1^+$. To overcome this limitation, conventional approaches using MRI have estimated the electrical properties of tissue using the transmit RF magnetic field $B_1^+$ for example, by mapping the amplitude of the transmit RF magnetic field and approximating the phase of the transmit magnetic field. Conventional MR-based electrical property measurement techniques typically rely on mapping the transmit RF field $B_1^+$, by attempting to eliminate the effect of the receive RF field $B_1^-$ from the MR images used for the measurements. The amplitude of $B_1^+$ can be obtained using various approaches, such as Bloch-Siegert $B_1^+$ mapping and/or the double-angle method. The phase of $B_1^+$, on the other hand, is generally more difficult to separate from the phase of the measured signal. Methods have been proposed to approximate the phase of $B_1^+$. Using conventional methods, a complex map of $B_1^+$ is formed and the map is subjected to Laplacian operation to produce $k^2$ (complex wave vector) maps and subsequently electrical properties maps.

While conventional approaches have provided techniques for estimating the electrical properties of tissue based on mapping the amplitude of $B_1^+$ and approximating the phase of $B_1^+$, implementations of the conventional $B_1^+$ mapping approaches may require specialized MRI sequences, not existing on all clinical scanners. Even if they exist on a scanner, these sequences tend to be signal to noise ratio (SNR) inefficient for the purpose of estimating electrical properties, requiring a rather lengthy acquisition time.

SUMMARY

Exemplary embodiments of the present disclosure are directed to estimating electrical properties of tissue, in-vivo, using a complex image; the complex value of each pixel of the image is proportional to a product of the transmit RF magnetic field and the receive magnetic field.

In one embodiment, a method of estimating an electrical property of tissue is disclosed. The method includes obtaining complex MR images of a target tissue. The method also includes determining an estimated value of an electrical property of the target tissue based on complex values of the pixels in the complex MR images. The complex values are proportional to product of the transmit RF magnetic field and the receive RF magnetic field.

In another embodiment, a non-transitory computer readable medium that stores instructions executable by a processing device is disclosed. Execution of the instructions by the computing device causes the processing device to implement a method for estimating electrical properties of tissue that includes obtaining complex MR images of a target tissue. Execution of the instructions by the processing device further causes the processing device to determine an estimated value of an electrical property of the target tissue based on complex values of the pixels in the complex MR images. The complex values are proportional to a product of the transmit RF magnetic field and the receive RF magnetic field.

In still another embodiment, a system for estimating electrical properties of tissue is disclosed. The system includes a non-transitory computer-readable medium and a processing device. The non-transitory computing readable medium stores complex MR images of a target tissue. The processing device is programmed to retrieve the complex MR images of the target tissue and determine an estimated value of an electrical property of the target tissue based on complex values of the pixels in the complex MR images. The complex values are proportional to the product of the transmit RF magnetic field and the receive RF magnetic field.

In exemplary embodiments, the complex values of the MR images are defined by a magnitude of MR images acquired using a gradient echo protocol and a phase of MR images acquired using a spin echo scanning protocol. The gradient echo image can have an excitation flip angle that is less than or equal to about ten degrees.

In exemplary embodiments, the electrical property can be at least one of the permittivity or the electrical conductivity of the target tissue and determining the electrical property can include calculating a Laplacian of the square root of the product, dividing the Laplacian by the square root of the product to generate a fractional Laplacian, obtaining a real value of the fractional Laplacian, and dividing the real value of the fractional Laplacian by a constant value to calculate the permittivity. The values of electrical property corresponding to the target tissue can be determined on a pixel-by-pixel basis and a map of the values of the electrical property can be generated using a calculation of the electrical property at each pixel.

In exemplary embodiments, a map of the electrical property of the target tissue can be generated and employed in conjunction with dynamic contrast-enhanced imaging of the target tissue to distinguish between malignant tissue regions and normal tissue regions based on values of the electrical property in the map.

In exemplary embodiments, simulations of MR acquisitions can be performed to extract maps for transmit and receive RF fields. The difference between the simulated values and the measured values can be identified. An accuracy of the estimated value of the electrical tissue properties can be determined based on the difference between the measured and simulated magnetic fields and/or an error range can be generated for the estimated values.

In exemplary embodiments, when using a transmit-receive RF coil and a low flip angle acquisition (for which the signal is proportional to the product $B_1^+$ times $B_1^+$), there is no need to separate the transmit and receive field in order to generate maps of tissue electrical properties. This is explained by Maxwell's equations. In certain geometries, the measurement is also quantitative. A combined "transceiver" amplitude is directly proportional to a low-flip-angle gradient echo (GRE) image intensity, and a combined "transceiver" phase is exactly the phase of a spin echo (SE) image. In exemplary embodiments a need for $B_1^+$ mapping can be eliminated and standard GRE and SE images can be used to generate tissue electrical properties maps. Experimental phantom tests indicate that exemplary embodiments of the present disclosure are valid for certain symmetric geometries and that exemplary embodiments of the present disclosure are at least as accurate in estimating electrical properties as conventional estimation techniques, while significantly reducing scan time and using a simplified workflow.

Any combination or permutation of embodiments is envisaged. Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

FIG. 3A illustrates a map of relative permittivity of phantoms consisting of spheres of salt water and oil using an exemplary embodiment of the process of FIG. 2.

FIG. 3B illustrates a map of electrical conductivity of phantoms consisting of spheres of salt water and oil using an exemplary embodiment of the process of FIG. 2.

FIG. 4A illustrate a map of relative permittivity of phantoms consisting of spheres of salt water and oil using a conventional B1 mapping process.

FIG. 4B illustrates a map of an electrical conductivity of phantoms consisting of spheres of salt water and oil using a conventional B1 mapping process

DESCRIPTION OF EXEMPLARY EMBODIMENTS

Exemplary embodiments of the present disclosure are directed to estimating electrical properties of tissue using a "transceive" amplitude and a "transceive" phase, where the term "transceive" herein refers a term that includes both the transmit RF magnetic field $B_1^+$ and the receive RF magnetic field $B_1^+$. For example, in exemplary embodiments, the transceive magnitude can be directly proportional to an intensity of a gradient echo MR image given by the product of the transmit RF field and the receive RF field ($B_1^+B_1^-$) and transceive phase can be the phase of a spin echo (SE) image defined by the transmit RF field and the receive RF field.

In exemplary embodiments, a low-flip-angle (e.g., a flip angle that is less than or equal to ten degrees) gradient echo (GRE) image can be acquired to determine the transceive amplitude. Exemplary embodiments advantageously use a relationship between the combined transceive amplitude and phase of MR images to compute tissue electrical properties from MR images without requiring dedicated $B_1$ mapping. Exemplary embodiments can advantageously calculate tissue electrical properties directly from a set of (gradient-echo and spin-echo) MR images such that standard MR imaging can be employed by exemplary embodiments to provide significantly more signal-to-noise ratio (SNR) efficiency than conventional $B_1$ mapping techniques and to provide precise and accurate tissue electrical properties maps that can be obtained faster than when using conventional $B_1$ mapping techniques.

Figure 1:
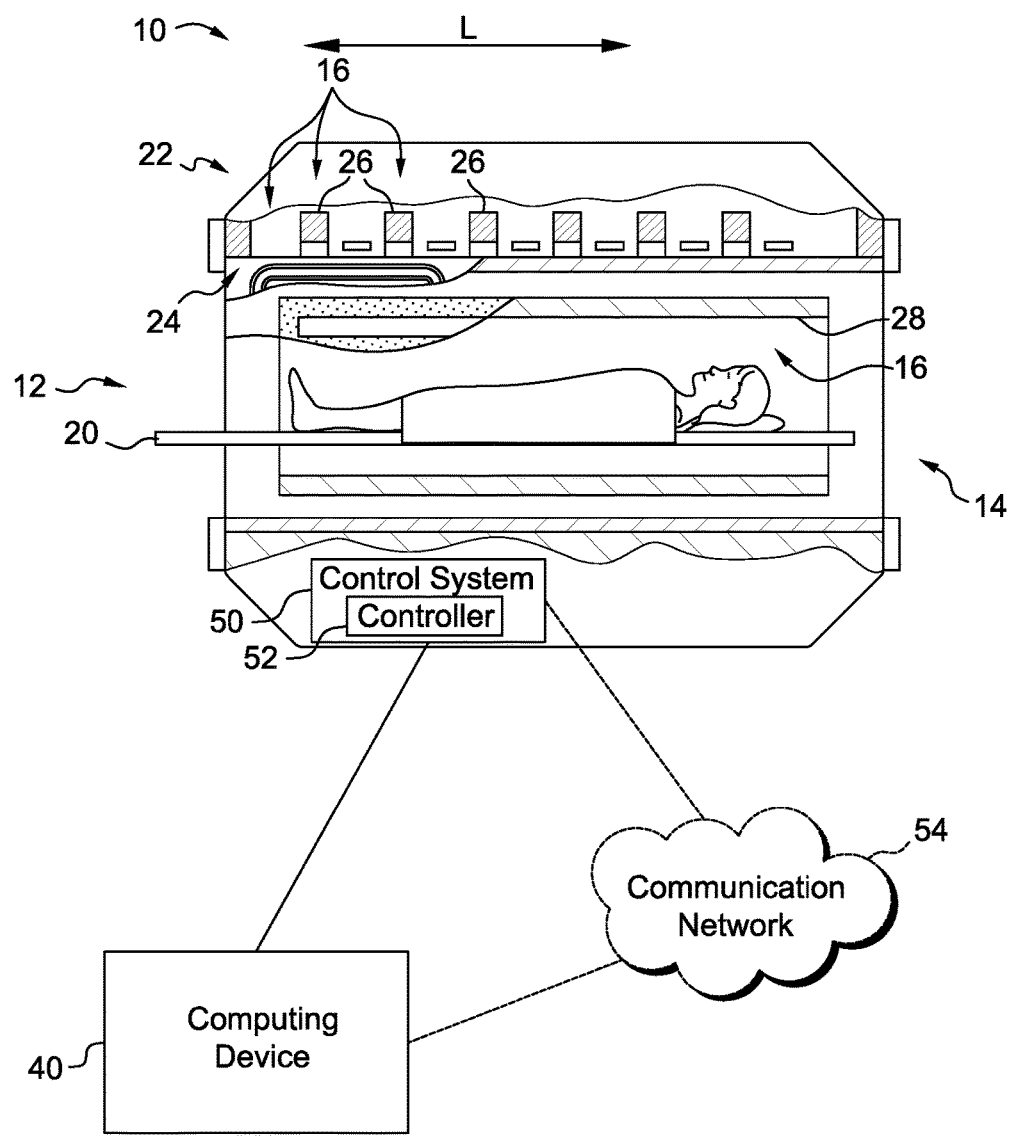
FIG. 1 illustrates an exemplary MRI scanner in accordance with exemplary embodiments of the present disclosure. Local RF coils that may be used (e.g. transmit/receive head coils) are not shown.

FIG. 1 is illustrative of a MRI scanner 10. The scanner 10 can generally extend longitudinally along a longitudinal axis L from a proximal end 12 to the distal end 14. The scanner 10 can include MRI components 16 forming an MRI scanner portion configured to acquire MR data. In some embodiments, the scanner 10 can be configured as a multi-modality imaging system. For example, the scanner 10 can be implemented as a combined medical imaging scanner configured to acquire MR image as well as Computed Tomography (CT) images, Positron Emission Tomography (PET) images, a Single Photon Emission Computed Tomography (SPECT) images, ultrasound images, and/or any other imaging modalities suitable for acquiring images of a subject.

The MRI components 16 can include a magnet assembly 22 and a gradient coil assembly 24, which can be implemented separately or as part of the magnet assembly 22. The magnet assembly 22 can include a polarizing main magnet 26 and a coil assembly 28, which can be implemented as a radio frequency (RF) coil and a phased array receive coil. The coil assembly 28 of the magnet assembly 22 can be configured to transmit stimulus pulses and to receive excitation pulses radiating from the subject in response to the stimulus pulses. The gradient assembly 24 can include one or more physical gradient coils (e.g., three gradient coils having orthogonal axes, X, Y, Z) to produce magnetic field gradients to spatially encode acquired MR data output from the scanner 10 according to a k-space or raw data matrix. In exemplary embodiments, one or more k-trajectories can be implemented, such as a Cartesian k-trajectory, spiral k-trajectory, cone k-trajectory, radial k-trajectory, and/or any other suitable k-trajectory.

Figure 7:
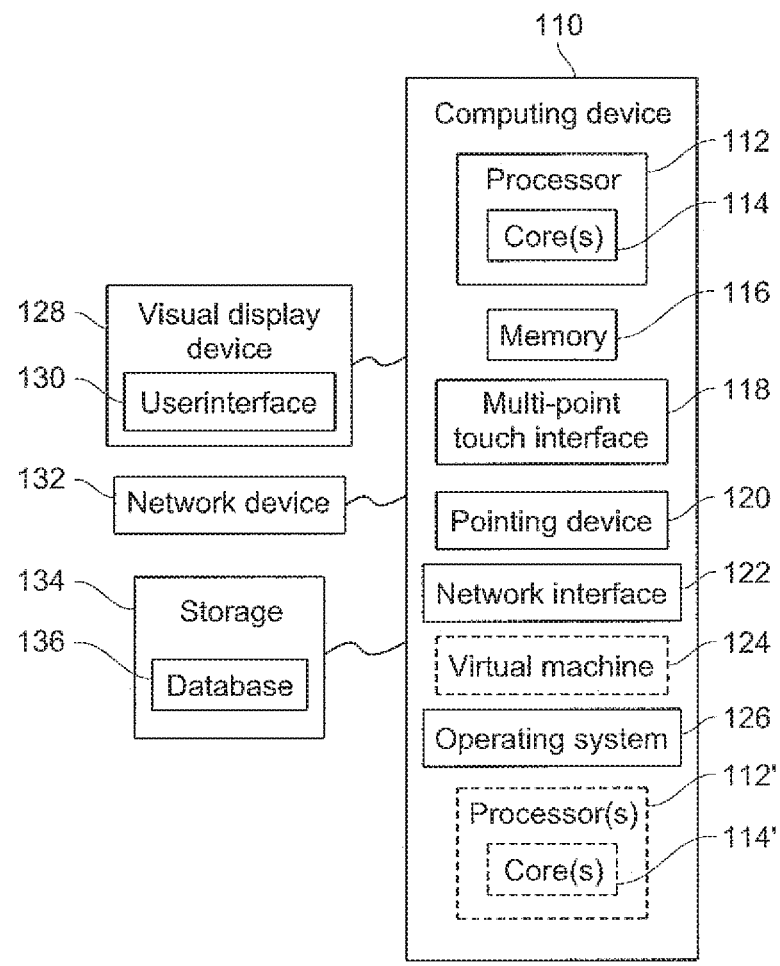
FIG. 7 is an exemplary computing device programmed and/or configured to implemented embodiments of the present disclosure.

In exemplary embodiments, the scanner 10 can include a control system 50 having processing device, e.g., controller 52, for controlling an operation of the scanner 10. The controller 52 of the control system 50 can be programmed to control an operation of the MRI components 16. While the control system 50 is depicted as being included in the scanner 10, those skilled in the art will recognize that the control system 50, or portions thereof, can be implemented separately and apart from the scanner 10 and can be communicatively coupled to the scanner 10. The control system 50 can be in communication with a computing device 40 such that the scanner 10 can be controlled, via a computing device 40 communicatively coupled to the control system 50, to transmit data and/or commands to the control system 50 to control an operation of the scanner 10. In some embodiments, the computing device 40 can be in communication with the control system 50 via a communications network 54. An exemplary computing device suitable for implementing the computing device 40 is shown in FIG. 7.

In exemplary embodiments, the computing device 40 can be configured and/or programmed to transmit instructions, commands, and/or requests to the control system 50 to control the MRI components 16 to perform scan sequences and can be programmed and/or configured to receive MR data or MR images from the control system 50. For example, RF pulses of a scan sequence for acquisition of MR images can have a timing, strength, and shape corresponding to a timing and length of a data acquisition window over which the MR data is to be acquired. Gradient pulses can be produced during the MR data acquisition by controlling one or more physical gradient coils (e.g., X, Y, Z coils) in a gradient coil assembly 24 to produce magnetic field gradients to spatially encode acquired MR data output from the scanner 10 in one or more lines of k-space. MR signals resulting from the excitation pulses, emitted by excited nuclei in a subject, can be sensed by the coil assembly 28, and can be provided to the computing system for processing. MR data can be collected and output as one or more sets of raw k-space data. The raw k-space data can be utilized in reconstruction (e.g., via Fourier transform) of MR image data by the computing device 40 and/or another device.

In exemplary embodiments, the computing device 40 (and/or the control system 50) can be programmed and/or configured to estimate electrical properties of a subject based on one or more MR data acquisitions. For example, the computing device 40 can be configured to estimate the permittivity and conductivity of at least a portion of a subject. In one embodiment, in-vivo measurements of living tissue, e.g., of a living human patient, can be used to estimate the permittivity and conductivity of the living tissue. In exemplary embodiments, the computing device 40 can be programmed and/or configured to estimate the electrical properties of tissue, e.g., permittivity and conductivity, based on one or more complex images formed from MR scans acquired using different scanning protocol. In some embodiments, the scanning protocols used to form the complex images can be standard scans, such as small flip angle gradient echo imaging scans and/or spin echo scans, which are generally available on MRI scanners.

The permittivity and electrical conductivity of human tissue are related to a spatial distribution of the transmit and receive RF magnetic field by the following equations:

$$\nabla^2 B_1^+ + k^2 B_1^+ = 0 \qquad (1)$$

$$\nabla^2 B_1^- + k^2 B_1^- = 0 \qquad (2),$$

where $$k^2 = \mu \epsilon_r \epsilon_0 \omega^2 - i\mu\sigma\omega. \qquad (3)$$

In the above equations, $B_1^+$ represents the complex amplitude of the radio frequency (RF) transmit magnetic field inside the tissue at a given three dimensional location and $B_1^-$ represents the complex amplitude of the RF receive magnetic field inside the tissue at the given three dimensional location. The variable $k^2$ represents the complex wave number, which can be defined by the electrical properties of $\mu$ (magnetic permeability), $\epsilon_r$ (relative permittivity), $\sigma$ (conductivity) at a frequency $\omega=2\pi f$. For mapping of tissue electrical properties, the magnetic permeability $\mu$ can be equated to the value in a vacuum, $\mu_0=4\pi\times10^{-7}$ [H/m]. The constant $\epsilon_0=8.854\times10^{-12}$ [F/m] is the permittivity of a vacuum.

Eqs. 1-3 above, can have limited use in practical in-vivo measurement of tissue electrical properties because in MRI, the phase of the complex amplitudes $B_1^+$ and $B_1^-$ are not directly accessible. What can be measured in MRI is an image, whose complex amplitude is expressible as $$I = I_0 f(B_1^+) B_1^-, \qquad (4)$$

where $I_0$ is a constant that depends on the tissue under study and is independent of the electrical properties and the RF field, and $f(B_1^+)$ is a function of the transmit RF field which depends on the imaging sequence. In case of a small-flip-angle gradient echo image, the image intensity satisfies the following mathematical expression:

$$|I_{GRE}| = I_0 |B_1^+ B_1^-|. \qquad (4)\ (5)$$

That is, the magnitude of the intensity of the gradient echo image ($I_{GRE}$) is equal to the magnitude of the product of the transmit RF field and the receive RF field multiplied by $I_0$. On the other hand, a spin echo image satisfies the following mathematical expression:

$$\angle I_{SE} = \angle(B_1^+ B_1^-). \qquad (5)\ (6)$$

That is, the phase of the spin echo image is equal to the phase of the product of the transmit RF field and the receive RF field. The phase of spin echo can be properly corrected against any artificial phase offset using a phantom scan, estimation, curve fitting, calibration, and/or any other suitable approaches to correct for phase offset. In some embodiments, spin echo (SE) images are acquired of a low-conductivity, low-permittivity phantom that is substantially larger than an imaged object with the same scan prescription to calibrate out any scanner or sequence specific image phase offset. This calibration can be performed when there is a reason to suspect change in such an offset and/or can be performed periodically. Using the image intensity from Eq. 5 and the phase from Eq. 6, a complex image can be formed combining the magnitude of the image intensity from the low flip angle (e.g., a flip angle that is less than or equal to ten degrees) gradient echo image with the phase from the spin echo image. Each pixel in this complex image can represent an image intensity $I_{COM}$ having complex values defined by the following mathematical expression:

$$I_{COM} = \sqrt{|I_{GRE}| * e^{i*\angle I_{SE}}} \quad (7)$$

$$I_{COM} = \sqrt{B_1^+ B_1^-}, \quad (8)$$

where i represents the imaginary unit (i.e., $i^2 = -1$), $B_1^+$ in Eq. 8 represents the complex transmit RF field and $B_1^-$ in Eq. 8 represents the complex receive RF field In exemplary embodiments, an equation relating the electrical properties of tissue with the product of complex amplitude of $B_1^+$ and $B_1^-$ from Eqs. 7 and 8 can be defined in accordance with exemplary embodiments and can be employed by the computing device 40 (and/or controller 52) to estimate the permittivity and conductivity of tissue in-vivo. The following mathematical expression can be derived from Eqs. 1-3.

$$\frac{\nabla^2 \sqrt{B_1^+ B_1^-}}{\sqrt{B_1^+ B_1^-}} + k^2 + \frac{1}{4}\left\|\nabla \ln \frac{B_1^-}{B_1^+}\right\|^2 = 0. \quad (6)(9)$$

The first term of Eq. 9 represents the fractional Laplacian of the square root of the product of the RF transmit and receive fields ($B_1^+ B_1^-$), where $\nabla^2(\_)$ is the Laplace operator. The first term (i.e., the fractional Laplacian) depends on a measureable quantity, namely the amplitude of the low-flip-angle gradient echo image and the phase of the spin-echo image. The third term is typically not directly measureable. However, in cases where this term is small compared to the complex wave number $k^2$, the electrical properties of tissue can be estimated by ignoring the third term and solving for $\Box_r$ and σ which can be represented as follows:

$$\epsilon_r \approx -\frac{1}{\mu \epsilon_0 \omega^2} \text{Re}\left(\frac{\nabla^2 \sqrt{B_1^+ B_1^-}}{\sqrt{B_1^+ B_1^-}}\right) \quad (10)$$

$$\sigma \approx \frac{1}{\mu \omega} \text{Im}\left(\frac{\nabla^2 \sqrt{B_1^+ B_1^-}}{\sqrt{B_1^+ B_1^-}}\right) \quad (11)$$

For an object with left-right (anterior-posterior) mirror symmetry, the sagittal (coronal) middle plane satisfies $B_1^+ = B_1^-$, and therefore, the third term of Eq. 9 is identically zero. Even if the third term of Eq. 9 is not negligible, provided that it has little spatial correlation with the distribution of the electrical properties, the third term can still be ignored and equations Eq. 10 or 11 can be evaluated by the computing device 40 (and/or controller 52) to reveal image contrast correlating primarily with the electrical properties of the tissue.

Exemplary embodiments of the computing device 40 (and/or control system 50) can be programmed and/or configured to process MR images using Eqs. 10 and 11 to determine electrical properties of tissue. For example, the computing device 40 can be programmed and/or configured to process MR images on a pixel-by-pixel basis and to estimate the electrical properties of the tissue from each pixel. Using this information, the computing device 40 (and/or controller 52) can generate a map of the electrical properties of the tissue.

Figure 2:
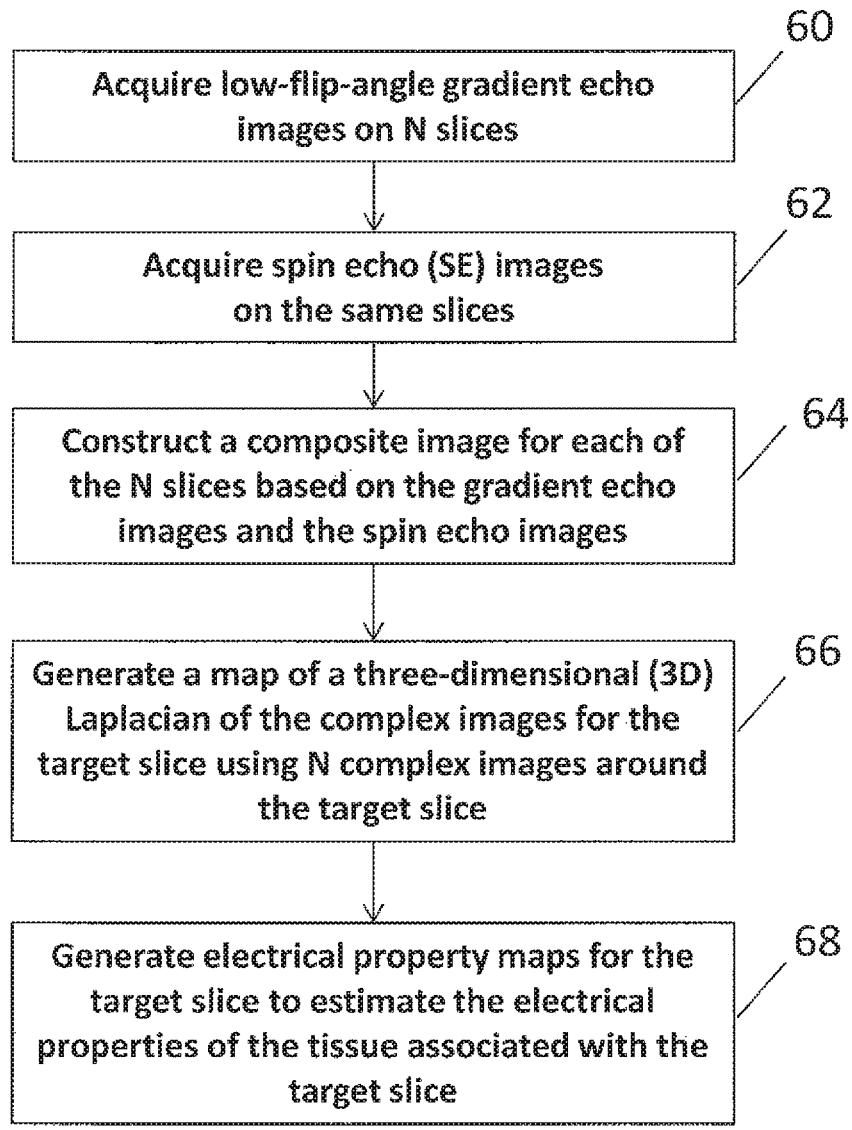
FIG. 2 is a flowchart illustrating an exemplary process for estimating electrical properties of tissue using a complex image.

FIG. 2 is a flowchart of an exemplary process implemented by the computing device 40 (FIG. 1) for estimating electrical properties (e.g., permittivity and electrical conductivity) of tissue using one or more MR images acquired by one or more MR scans. To estimate the electrical properties, permittivity or conductivity, N slices are acquired with at least two scanning protocols with a slice spacing S centered around the slice on which measurement of the electrical properties is desired (target slice). In exemplary embodiments, at least three slices are acquired (N≥3) and the slice spacing is generally uniform, e.g., approximately 3 mm spacing in some embodiments. In the present embodiment, low-flip-angle (e.g., a flip angle that is less than or equal to ten degrees) gradient echo (GRE) images are acquired on the N slices by the scanner 10 in response to instructions received from the computing device (60) and spin echo (SE) images are acquired on the same slices by the scanner 10 in response to instructions received from the computing device (62). In some embodiments, calibration SE images are acquired of a low-conductivity, low-permittivity phantom that is substantially larger than the imaged object with the same scan prescription to calibrate out any scanner—or pulse sequence (psd)—specific image phase offset. These calibration scans can be performed when there is a reason to suspect change in such an offset and/or can be performed periodically.

The computing device 40 can be programmed and/or configured to construct a composite image for each of the N slices based on the gradient echo images and the spin echo images (64). In exemplary embodiments, the composite image can be constructed as described herein with respect to Eqs. 5-8 such that each pixel of the composite complex image can be represented by a complex value that is proportional to the product of the transmit RF magnetic field and the receive RF magnetic field corresponding to the tissue represented by that pixel. A map of a three-dimensional (3D) Laplacian of the complex image is programmatically generated by the computing device 40 for the target slice using N complex images around the target slice (66). This 3D Laplacian map can be generated using one of various known methods to estimate Laplacian of a 3-dimensional data with noise. For example, the Laplacian may be estimated using curve fitting by, e.g., fitting a second order polynomial to the complex image data in a piecewise manner in each dimension (X, Y, Z). In some embodiments, filtering, averaging, and/or regression techniques can be applied to suppress noise propagation in associated with the differentiation.

The computing device can be programmed and/or configured to generate electrical property maps for the target slice to estimate the electrical properties of the tissue associated with the target slice (68). The computing device 40 can be programmed and/or configured to generate the electrical property maps by evaluating Eqs. 10 and/or 11 on a pixel-by-pixel basis for the target slice. The electrical property maps generated by the computing device can be output to an output device, such as a display device or a printer, and/or can be stored in a non-transitory computer-readable medium. For example, the electrical property maps can be rendered on a display unit (FIG. 7) so that an operator may view and/or analyze the electrical properties of tissue associated with the acquired images.

Exemplary embodiments of the present disclosure advantageously allow in-vivo mapping of tissue electrical properties that would not have been possible using standard MRI scans, such as gradient or spin echo. Quantitative measurement of such electrical properties can be used for more accurate RF safety assessment and RF hyperthermia treatment planning. Quantitative, semi-quantitative or qualitative estimation (such as low/medium/high) can also advantageously provide diagnostic value. For example, permittivity and/or conductivity contrast can help discriminate between benign and malignant tissues; such separation is sometimes not clear using standard acquisition techniques, with or without contrast agents. Furthermore, exemplary embodiments of the present disclosure can be advantageously implemented without dedicated $B_1$ mapping sequences. Such $B_1$ mapping sequences can be time consuming and/or SAR intensive. Moreover, exemplary embodiments permit estimating of electrical properties using gradient echo imaging and spin echo imaging, which generally provide more SNR efficiency than $B_1$ mapping. As a consequence, more accurate and precise permittivity and conductivity measurements are possible using the current approach than when using conventional $B_1$ mapping techniques. Exemplary embodiments of the present disclosure can be implemented as a fast (<5 min) protocol based on standard GRE and SE scans with limited user intervention.

FIGS. 3A and 3B illustrate exemplary electrical property maps 70 and 71, respectively. FIGS. 4A and 4B illustrate exemplary electrical property maps 72 and 73. The maps 70 and 72 correspond to a relative permittivity and the maps 71 and 73 correspond to conductivity. The relative permittivity and conductivity were measured in a phantom experiment to demonstrate an application of exemplary embodiments applied to an axial slice of a three-sphere phantom in which the third term of Eq. 9 is not zero. The phantoms used to generate the maps of FIGS. 3A, 3B, 4A, and 4B include a salt water sphere 74 having a first concentration of salt, a salt water sphere 75 having a second concentration of salt, and a sphere 76 filled with oil. As shown in FIGS. 3 and 4, despite the influence of the third term to the estimation of the electrical properties in FIGS. 3A and 3B, exemplary embodiments facilitate accurate mapping of permittivity $\epsilon_r$ and conductivity $\sigma$ compared to conventional B1 mapping techniques shown in FIGS. 4A and 4B.

Figure 5:
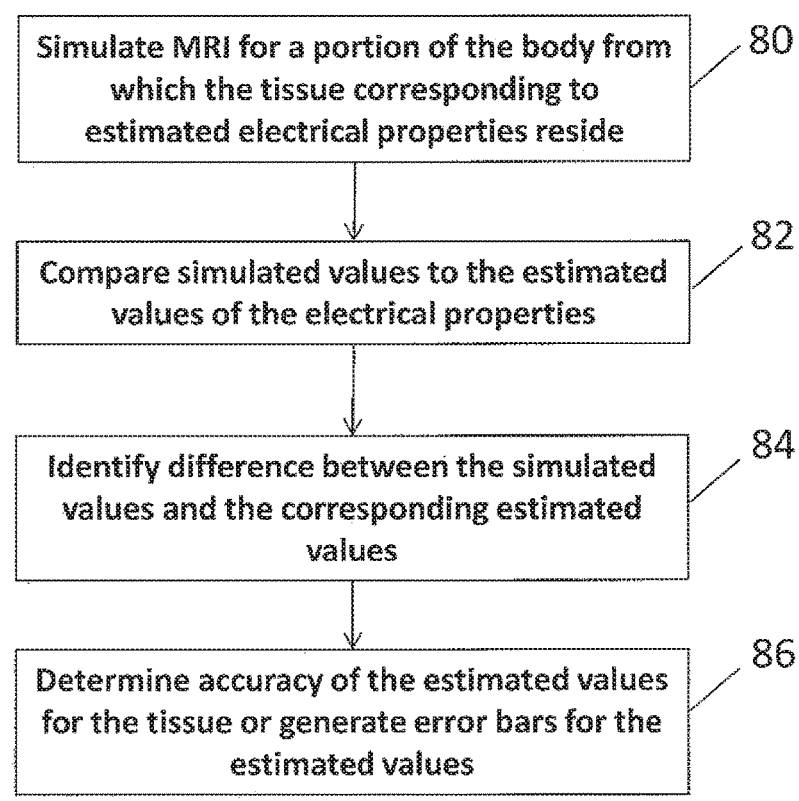
FIG. 5 is a flowchart of an exemplary process for determining an error associated with estimating electrical properties obtained via an exemplary embodiment of the process of FIG. 2.

FIG. 5 is a flowchart illustrating an exemplary process of estimating errors in the conductivity and permittivity based on the process of FIG. 3 and adjusting for such errors. By using the complex image, which includes both $B_1^+$ and $B_1^-$, exemplary embodiments allow for determining the accuracy of the estimation which can be examined by, for example, human-model RF simulation for a particular anatomy. To begin, computing device 40 can be programmed and/or configured to perform a simulation corresponding to the portion of the body from which the tissue corresponding to the acquired images resides (80). The simulation can use the anatomical information from prior MRI series and predetermined stored values for the electrical properties of the tissue. For example, electrical properties of bone, muscle, and fat can be stored for use in simulations. Exemplary embodiments can be implemented using commercially available MRI simulation software including, but not limited to, for example, SEMCAD from Schmid & Partner Engineering AG, XFdtd from Remcom, HFSS from Ansys, and/or any other suitable simulation software for modeling or simulating electrical properties of tissue.

The results of the simulations (complex values for the $B_1^+$ and $B_1^-$ quantities) can be used to compute the error term (last term) of Equation 9, and adjust the assessment of conductivity and permittivity (Equations 10 and 11) according to this error term.

Figure 6:
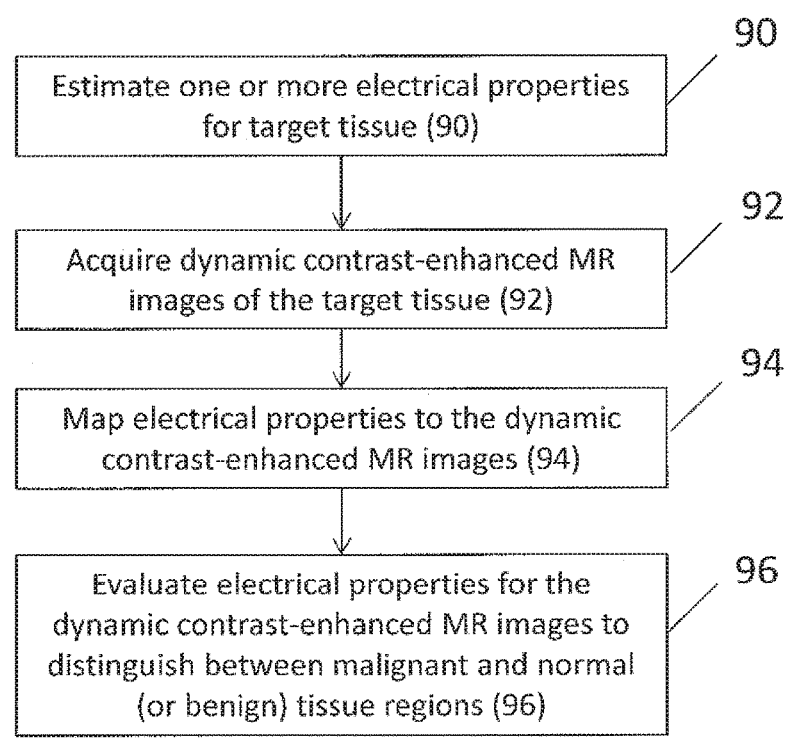
FIG. 6 is a flowchart of an exemplary process for discriminating between malignant tissue and normal tissue based on an estimation of electrical properties using an exemplary embodiment of the process of FIG. 2.

FIG. 6 is a flowchart of an exemplary process for discriminating between malignant tissue and normal (or benign) tissue in acquired MR images. One or more electrical properties (e.g., permittivity and conductivity) are estimated for target tissue based on an embodiment of the process described herein with reference to FIG. 2 (90). Additionally, dynamic contrast-enhanced MR imaging of the target tissue is acquired (92). The values of one or more electrical properties are mapped to the dynamic contrast-enhanced MR images to associate the values of the one or more electrical properties with corresponding pixels of the dynamic contrast-enhanced MR images (94). The values of the electrical properties are evaluated for the dynamic contrast-enhanced MR images to distinguish between malignant and normal (or benign) tissue regions (96). For example, it may be difficult to distinguish whether a tumor is malignant or benign using the dynamic contrast-enhanced MR images. By mapping or super-imposing the estimated values of the electrical properties to the dynamic contrast-enhanced MR images, the relationship between the electrical properties and composition of tissue can be used to determine whether the tumor is malignant. For example, malignant tissue has been shown to have a permittivity value that is greater than the permittivity of normal (or benign) tissue.

FIG. 7 is a block diagram of an exemplary computing device 110 that may be used to implement exemplary embodiments of the computing device 40. The computing device 110 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 116 included in the computing device 110 may store computer-readable and computer-executable instructions or software for interface with and/or controlling an operation of the scanner 10. The computing device 110 also includes configurable and/or programmable processor 112 and associated core 114, and optionally, one or more additional configurable and/or programmable processing devices, e.g., processor(s) 112' and associated core(s) 114' (for example, in the case of computer systems having multiple processors/cores), for executing computer-readable and computer-executable instructions or software stored in the memory 116 and other programs for controlling system hardware. Processor 112 and processor(s) 112' may each be a single core processor or multiple core (114 and 114') processor.

Virtualization may be employed in the computing device 110 so that infrastructure and resources in the computing device may be shared dynamically. A virtual machine 124 may be provided to handle a process running on multiple processors so that the process appears to be using only one computing resource rather than multiple computing resources. Multiple virtual machines may also be used with one processor.

Memory 116 may include a computer system memory or random access memory, such as DRAM, SRAM, EDO RAM, and the like. Memory 116 may include other types of memory as well, or combinations thereof.

A user may interact with the computing device 110 through a visual display device 128, such as a computer monitor, which may display one or more user interfaces 130 that may be provided in accordance with exemplary embodiments. The computing device 110 may include other I/O devices for receiving input from a user, for example, a keyboard or any suitable multi-point touch interface 118, a pointing device 120 (e.g., a mouse). The keyboard 118 and the pointing device 120 may be coupled to the visual display device 128. The computing device 110 may include other suitable conventional I/O peripherals.

The computing device 110 may also include one or more storage devices 134, such as a hard-drive, CD-ROM, or other computer readable media, for storing data and computer-readable instructions and/or software that interface with and/or control an operation of the scanner 10 described herein and/or to implement exemplary processes described herein with reference to FIGS. 2, 5, and 6. Exemplary storage device 134 may also store one or more databases for storing any suitable information required to implement exemplary embodiments. For example, exemplary storage device 134 can store one or more databases 136 for storing information, such as scan sequences, MR data, MR images, estimation of electrical properties, electrical property maps, and/or any other information that can be used to implement exemplary embodiments of the present disclosure. The databases may be updated by manually or automatically at any suitable time to add, delete, and/or update one or more items in the databases.

The computing device 110 can include a network interface 122 configured to interface via one or more network devices 132 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 122 may include a built-in network adapter, network interface card, PCMCIA network card, card bus network adapter, wireless network adapter, USB network adapter, modem or any other device suitable for interfacing the computing device 110 to any type of network capable of communication and performing the operations described herein. Moreover, the computing device 110 may be any computer system, such as a workstation, desktop computer, server, laptop, handheld computer, tablet computer, or other form of computing or telecommunications device that is capable of communication and that has sufficient processor power and memory capacity to perform the operations described herein.

The computing device 110 may run any operating system 126, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 126 may be run in native mode or emulated mode. In an exemplary embodiment, the operating system 126 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A method of estimating an electrical property of tissue comprising:
   obtaining complex Magnetic Resonance (MR) images of a target tissue; and
   determining an estimated value of an electrical property of the target tissue based on complex values of the pixels in the complex MR images, the complex values being proportional to a product of the transmit RF magnetic field and the receive RF magnetic field;
wherein the electrical property is a permittivity or electrical conductivity of the target tissue and wherein determining the permittivity or electrical conductivity further comprises: calculating a Laplacian of a square root of the product of the transmit and received RF field; and dividing the Laplacian by the square root of the product to generate a fractional Laplacian.

2. The method of claim 1, wherein the magnitude of the product of the transmit RF magnetic field and the receive RF magnetic field is obtained from the intensity of MR images acquired using a gradient echo protocol.

3. The method of claim 2, wherein the gradient echo images have an excitation flip angle that is less than or equal to about ten degrees.

4. The method of claim 1, wherein the phase of the product of the transmit RF magnetic field and the receive RF magnetic field is obtained from the phase of MR images acquired using a spin echo scanning protocol.

5. The method of claim 1, wherein determining the permittivity further comprises:
   obtaining a real value of the fractional Laplacian; and
   dividing the real value of the fractional Laplacian by a constant value to calculate the permittivity.

6. The method of claim 5, wherein the permittivity of the target tissue is determined on a pixel-by-pixel basis and wherein the method further comprises:
   generating a map of the permittivity of the target tissue using a calculation of the permittivity at each pixel.

7. The method of claim 1, wherein determining the conductivity further comprises: obtaining an imaginary value of the fractional Laplacian; and
   dividing the imaginary value of the fractional Laplacian by a constant value.

8. The method of claim 7, wherein the conductivity corresponding to the target tissue is determined on a pixel-by-pixel basis and wherein the method further comprises:
   generating a map of the conductivity of the in-vivo tissue using a calculation of the electrical conductivity at each pixel.

9. The method of claim 1, further comprising:
   generating a map of the electrical property of the target tissue;
   and distinguishing between malignant tissue regions and normal tissue regions based on values of the electrical property in the map.

10. The method of claim 9, further comprising:
employing the map in conjunction with dynamic contrast-enhanced imaging of the target tissue before distinguishing between malignant tissue regions and normal tissue regions.

11. A method of estimating an electrical property of tissue comprising:
obtaining complex Magnetic Resonance (MR) images of a target tissue;
determining an estimated value of an electrical property of the target tissue based on complex values of the pixels in the complex MR images, the complex values being proportional to a product of the transmit RF magnetic field and the receive RF magnetic field;
simulating MR acquisitions to obtain spatially resolved simulated values for the transmit and receive RF fields; and
adjusting the previously computed values of conductivity and permittivity based on the squared norm of the gradient of the natural logarithm of the simulated $B_1^-/B_1^+$ ratio.

12. A non-transitory computer readable medium storing instructions, wherein execution of the instruction by a processing device causes the processing device to implement a method for estimating electrical properties of tissue comprising:
obtaining complex Magnetic Resonance (MR) images of a target tissue; and
determining an estimated value of an electrical property of the target tissue based on complex values of the pixels in the complex MR images, the complex values being proportional to a product of the transmit RF magnetic field and the receive RF magnetic field;
wherein the electrical property is at least one of permittivity or electrical conductivity of the target tissue and wherein determining the electrical property further comprises:
calculating a Laplacian of the square root of the product of the transmit and received RF field;
dividing the Laplacian by the square root of the product of the transmit and received RF field to generate a fractional Laplacian;
obtaining one of a real value or an imaginary value of the fractional Laplacian; and
dividing the one of the real value or the imaginary value of the fractional Laplacian by a constant value to calculate the electrical property.

13. The medium of claim 12, wherein the magnitude of the product between the transmit RF magnetic field and the receive RF magnetic field is obtained from the intensity of MR images acquired using a gradient echo protocol and the phase of the product between the transmit and receive RF magnetic fields is obtained from the phase of images acquired using a spin echo scanning protocol.

14. A system for estimating electrical properties of tissue comprising:
a non-transitory computing readable medium storing complex MR images of a target tissue; and
a processing device programmed to retrieve the complex MR images of the target tissue and determine an estimated value of an electrical property of the target tissue based on complex values of pixels in the complex MR images, the complex values being proportional to a product of the transmit RF magnetic field and the receive RF magnetic field;
wherein the electrical property is at least one of permittivity and electrical conductivity of the target tissue and wherein the processing device is programmed to determine the electrical property by:
calculating a Laplacian of the square root of the product of the transmit and received RF field; and
dividing the Laplacian by the square root of the product of the transmit and received RF field to generate a fractional Laplacian
obtaining one of a real value or an imaginary value of the fractional Laplacian; and
dividing the one of the real value or the imaginary value of the fractional Laplacian by a constant value to calculate the electrical property.

15. The system of claim 14, wherein the magnitude of the product of the transmit RF magnetic field and the receive RF magnetic field is obtained from the intensity of MR images acquired using gradient echo protocol.

16. The system of claim 14, wherein the phase of the product between the product of the transmit and receive RF field is obtained from the phase of images acquired using a spin echo scanning protocol.

* * * * *